US010597407B2

(12) United States Patent
Lazarev

(10) Patent No.: US 10,597,407 B2
(45) Date of Patent: *Mar. 24, 2020

(54) ENERGY STORAGE MOLECULAR MATERIAL, CRYSTAL DIELECTRIC LAYER AND CAPACITOR

(71) Applicant: Capacitor Sciences Incorporated, Menlo Park, CA (US)

(72) Inventor: Pavel Lazarev, Menlo Park, CA (US)

(73) Assignee: CAPACITOR SCIENCES INCORPORATED, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/944,517

(22) Filed: Apr. 3, 2018

(65) Prior Publication Data

US 2018/0222924 A1 Aug. 9, 2018

Related U.S. Application Data

(62) Division of application No. 14/719,072, filed on May 21, 2015, now Pat. No. 9,932,358.

(51) Int. Cl.
| C07D 519/00 | (2006.01) |
| H01G 4/14 | (2006.01) |
| H01G 4/012 | (2006.01) |

(52) U.S. Cl.
CPC ........... *C07D 519/00* (2013.01); *H01G 4/012* (2013.01); *H01G 4/14* (2013.01)

(58) Field of Classification Search
CPC .................................................. C07D 519/00
USPC ........................................................ 546/28
See application file for complete search history.

(56) References Cited

U.S. PATENT DOCUMENTS

| 4,549,034 A | 10/1985 | Sato et al. |
| 5,597,661 A | 1/1997 | Takeuchi et al. |
| 6,519,136 B1 | 2/2003 | Chu et al. |
| 7,342,755 B1 | 3/2008 | Horvat et al. |
| 7,625,497 B2 | 12/2009 | Carson et al. |
| 7,678,907 B2 | 3/2010 | Koenemann et al. |
| 7,990,679 B2 | 8/2011 | Ehrenberg et al. |
| 8,766,566 B2 | 7/2014 | Baba et al. |
| 8,831,805 B2 | 9/2014 | Izumi et al. |
| 9,899,150 B2 | 2/2018 | Lazarev et al. |
| 9,916,931 B2 | 3/2018 | Lazarev |
| 9,978,517 B2 | 5/2018 | Lazarev et al. |
| 10,153,087 B2 | 12/2018 | Lazarev et al. |
| 2003/0105365 A1 | 6/2003 | Smith et al. |
| 2003/0160595 A1 | 8/2003 | Provanzana et al. |
| 2004/0223291 A1 | 11/2004 | Naito et al. |
| 2007/0003781 A1 | 1/2007 | Rochemont |
| 2007/0181973 A1 | 8/2007 | Hung et al. |
| 2008/0002329 A1 | 1/2008 | Pohm et al. |
| 2008/0283283 A1 | 11/2008 | Abe et al. |
| 2009/0184355 A1 | 7/2009 | Brederlow et al. |
| 2010/0011656 A1 | 1/2010 | Gessner et al. |
| 2010/0172066 A1 | 7/2010 | Baer et al. |
| 2011/0149393 A1 | 6/2011 | Nokel et al. |
| 2012/0008251 A1 | 1/2012 | Yu et al. |
| 2012/0059307 A1 | 3/2012 | Harris et al. |
| 2013/0056720 A1 | 3/2013 | Kim et al. |
| 2013/0224473 A1 | 8/2013 | Tassell et al. |
| 2014/0035100 A1 | 2/2014 | Cho |
| 2014/0036410 A1 | 2/2014 | Okamatsu et al. |
| 2014/0058080 A1 | 2/2014 | Lazarev |
| 2014/0316387 A1 | 10/2014 | Harris et al. |
| 2015/0008671 A1 | 1/2015 | Rentero et al. |
| 2015/0235769 A1 | 8/2015 | Carver et al. |
| 2016/0001662 A1 | 1/2016 | Miller et al. |
| 2017/0133167 A1 | 5/2017 | Keller et al. |
| 2017/0232853 A1 | 8/2017 | Lazarev et al. |
| 2017/0236641 A1 | 8/2017 | Furuta et al. |
| 2017/0236642 A1 | 8/2017 | Furuta et al. |
| 2017/0301467 A1 | 10/2017 | Lazarev et al. |
| 2018/0033554 A1 | 2/2018 | Li et al. |
| 2018/0061582 A1 | 3/2018 | Furuta et al. |
| 2018/0122143 A1 | 5/2018 | Ellwood |
| 2018/0126857 A1 | 5/2018 | Kelly-Morgan |
| 2018/0137978 A1 | 5/2018 | Hein et al. |
| 2018/0137984 A1 | 5/2018 | Furuta et al. |
| 2018/0158616 A1 | 6/2018 | Lazarev et al. |

FOREIGN PATENT DOCUMENTS

| CN | 1582506 A | 2/2005 |
| CN | 101541890 A | 9/2009 |
| CN | 1748271 B | 6/2010 |
| CN | 103258656 B | 8/2015 |
| EP | 2108673 A1 | 10/2009 |
| EP | 1990682 B1 | 1/2015 |
| JP | 2001093778 A | 4/2001 |
| JP | 2007532758 A | 11/2007 |
| JP | 2010504952 A | 2/2010 |

(Continued)

OTHER PUBLICATIONS

Extended European Search Report dated Aug. 8, 2018 for European Patent Application No. 16756391.5.
Extended European Search Report dated Sep. 24, 2018 for European Patent Application No. 15856609.1.
Extended European Search Report dated Sep. 26, 2018 for European Patent Application No. 16797411.2.
Final Office Action for U.S. Appl. No. 15/043,247, dated Oct. 24, 2018.

(Continued)

*Primary Examiner* — Taofiq A Solola

(74) *Attorney, Agent, or Firm* — BCF LLP

(57) ABSTRACT

The present disclosure provides an energy storage molecular material, crystal dielectric layer and capacitor which may solve a problem of the further increase of volumetric and mass density of reserved energy associated with some energy storage devices, and at the same time reduce cost of materials.

2 Claims, 1 Drawing Sheet

(56) References Cited

FOREIGN PATENT DOCUMENTS

| WO | 2009144205 A1 | 12/2009 |
| --- | --- | --- |
| WO | 2011137137 A1 | 11/2011 |
| WO | 2012142460 A1 | 10/2012 |
| WO | 2013085467 A1 | 6/2013 |

OTHER PUBLICATIONS

Final Office Action for U.S. Appl. No. 15/043,315, dated Jun. 7, 2018.
Final Office Action for U.S. Appl. No. 15/449,587, dated Oct. 10, 2018.
Final Office Action for U.S. Appl. No. 15/710,587, dated Nov. 6, 2018.
M. Jurow et al, "Porphyrins as molectular electronic components of functional devices", Coordination Chemistry Reviews, Elsevier Science, Amsterdam NL, vol. 254, No. 19-20, Oct. 1, 2010, pp. 2297-2310.
Non-Final Office Action for U.S. Appl. No. 15/043,247, dated Feb. 19, 2019.
Non-Final Office Action for U.S. Appl. No. 15/043,247, dated Jun. 7, 2018.
Non-Final Office Action for U.S. Appl. No. 15/430,339, dated Jul. 11, 2018.
Non-Final Office Action for U.S. Appl. No. 15/430,307, dated Jul. 16, 2018.
Non-Final Office Action for U.S. Appl. No. 15/449,587, dated May 21, 2018.
Non-Final Office Action for U.S. Appl. No. 15/710,587, dated Jul. 3, 2018.
Non-Final Office Action for U.S. Appl. No. 15/782,752, dated Sep. 21, 2018.
Non-Final Office Action for U.S. Appl. No. 15/801,240, dated Oct. 19, 2018.
Non-Final Office Action for U.S. Appl. No. 15/805,016, dated Jun. 4, 2018.
Non-Final Office Action for U.S. Appl. No. 15/870,504, dated Feb. 27, 2019.
Non-Final/Final Office Action for U.S. Appl. No. 15/430,391, dated Jul. 20, 2018.
Notice of Allowance for U.S. Appl. No. 15/043,315, dated Feb. 21, 2019.
Notice of Allowance for U.S. Appl. No. 15/043,315, dated Jan. 15, 2019.
Notice of Allowance for U.S. Appl. No. 15/163,595, dated Jul. 30, 2018.
Notice of Allowance for U.S. Appl. No. 15/449,524, dated Feb. 21, 2019.
Notice of Allowance for U.S. Appl. No. 15/710,587, dated Jan. 24, 2019.
Notice of Allowance for U.S. Appl. No. 15/782,752, dated Feb. 25, 2019.
Notice of Allowance for U.S. Appl. No. 15/801,240, dated Feb. 11, 2019.
Office Action dated May 18, 2018 for Chinese Patent Application for Invention No. 201580025110.
Office Action dated Jan. 29, 2019 for Japanese Patent Application No. 2017-512654.
Supplementary Notice of Allowance for U.S. Appl. No. 14/752,600, dated Dec. 4, 2017.
Taiwanese Office Action for 886103 Application No. 106142206, dated Jul. 5, 2018.
English translation of the abstract of JP 2007532758.
English translation of the abstract of JP 2010504952.
English translation of the abstract of CN 101541890.
Office Action dated Jun. 25, 2019 in corresponding Japanese application No. 2017-558522.

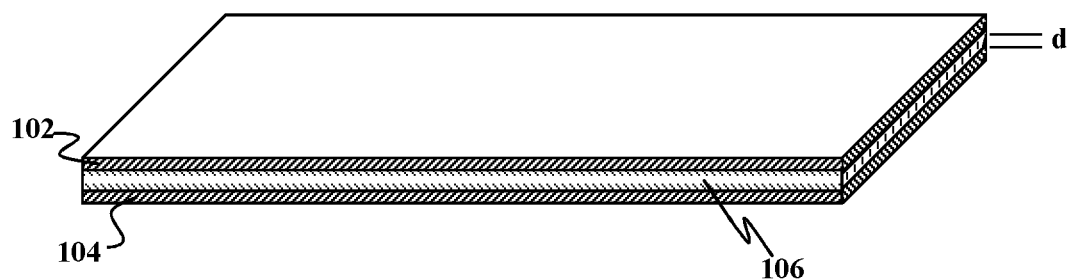

ENERGY STORAGE MOLECULAR MATERIAL, CRYSTAL DIELECTRIC LAYER AND CAPACITOR

CLAIM OF PRIORITY

This application is a divisional of U.S. patent application Ser. No. 14/719,072, filed May 21, 2015, the entire contents of which are incorporated herein by reference.

BACKGROUND

A capacitor is a passive electronic component that is used to store energy in the form of an electrostatic field, and comprises a pair of electrodes separated by a dielectric layer. When a potential difference exists between two electrodes, an electric field is present in the dielectric layer. An ideal capacitor is characterized by a single constant value of capacitance. This is a ratio of the electric charge on each electrode to the potential difference between them. In practice, the dielectric layer between electrodes passes a small amount of leakage current. Electrodes and leads introduce an equivalent series resistance, and dielectric layer has limitation to an electric field strength which results in a breakdown voltage. The simplest energy storage device consists of two parallel electrodes separated by a dielectric layer of permittivity $\varepsilon$, each of the electrodes has an area S and is placed on a distance d from each other. Electrodes are considered to extend uniformly over an area S, and a surface charge density can be expressed by the equation: $\pm\rho=\pm Q/S$. As the width of the electrodes is much greater than the separation (distance) d, an electrical field near the centre of the capacitor will be uniform with the magnitude $E=\rho/\varepsilon$. Voltage is defined as a line integral of the electric field between electrodes. An ideal capacitor is characterized by a constant capacitance C, defined by the formula (1)

$$C=Q/V, \quad (1)$$

which shows that capacitance increases with area and decreases with distance. Therefore the capacitance is largest in devices made of materials of high permittivity.

A characteristic electric field known as the breakdown strength $E_{bd}$, is an electric field in which the dielectric layer in a capacitor becomes conductive. The voltage at which this occurs is called the breakdown voltage of the device, and is given by the product of dielectric strength and separation between the electrodes, $$V_{bd}=E_{bd}d \quad (2)$$

The maximal volumetric energy density stored in the capacitor is limited by the value proportional to $\sim\varepsilon\cdot E^2_{bd}$, where $\varepsilon$ is dielectric permittivity and $E_{bd}$ is breakdown strength. Thus, in order to increase the stored energy of the capacitor it is necessary to increase dielectric permeability $\varepsilon$ and breakdown strength $E_{bd}$ of the dielectric.

Breakdown of the dielectric layer usually occurs when the intensity of the electric field becomes high enough to "pull" electrons from atoms of the energy storage molecular material and make them conduct an electric current from one electrode to another. Presence of impurities in the energy storage molecular material or imperfections of the crystal dielectric layer can result in an avalanche breakdown as observed in capacitor.

Other important characteristic of an energy storage molecular material is its dielectric permittivity. Different types of energy storage molecular materials are used for capacitors and include ceramics, polymer film, paper, and electrolytic capacitors of different kinds. The most widely used film materials are polypropylene and polyester. Increase of dielectric permittivity allows increasing of volumetric energy density which makes it an important technical task.

An ultra-high dielectric constant composite of polyaniline, PANI-DBSA/PAA, was synthesized using in situ polymerization of aniline in an aqueous dispersion of polyacrylic acid (PAA) in the presence of dodecylbenzene sulfonate (DBSA) (see, Chao-Hsien Hoa et al., "High dielectric constant polyaniline/poly(acrylic acid) composites prepared by in situ polymerization", Synthetic Metals 158 (2008), pp. 630-637). The water-soluble PAA served as a polymeric stabilizer, protecting the PANI particles from macroscopic aggregation. A very high dielectric constant of ca. $2.0*10^5$ (at 1 kHz) was obtained for the composite containing 30% PANI by weight. Influence of the PANI content on the morphological, dielectric and electrical properties of the composites was investigated. Frequency dependence of dielectric permittivity, dielectric loss, loss tangent and electric modulus were analyzed in the frequency range from 0.5 kHz to 10 MHz. SEM micrograph revealed that composites with high PANI content (i.e., 20 wt %) consisted of numerous nano-scale PANI particles that were evenly distributed within the PAA matrix. High dielectric constants were attributed to the sum of the small capacitors of the PANI particles. The drawback of this material is a possible occurrence of percolation and formation of at least one continuous conductive path under electric field with probability of such an event increasing with an increase of the electric field. When at least one continuous path (track) through the neighboring conducting PANI particles is formed between electrodes of the capacitor, it makes a breakdown voltage of such a capacitor being relatively low.

Single crystals of doped aniline oligomers are produced via a simple solution-based self-assembly method (see, Yue Wang, et. al., "Morphological and Dimensional Control via Hierarchical Assembly of Doped Oligoaniline Single Crystals", J. Am. Chem. Soc. 2012, 134, pp. 9251-9262). Detailed mechanistic studies reveal that crystals of different morphologies and dimensions can be produced by a "bottom-up" hierarchical assembly where structures such as one-dimensional (1-D) nanofibers can be aggregated into higher order architectures. A large variety of crystalline nanostructures, including 1-D nanofibers and nanowires, 2-D nanoribbons and nanosheets, 3-D nanoplates, stacked sheets, nanoflowers, porous networks, hollow spheres, and twisted coils, can be obtained by controlling the nucleation of the crystals and the non-covalent interactions between the doped oligomers. These nanoscale crystals exhibit enhanced conductivity compared to their bulk counterparts as well as interesting structure—property relationships such as shape-dependent crystallinity. Furthermore, the morphology and dimension of these structures can be largely rationalized and predicted by monitoring molecule—solvent interactions via absorption studies. Using doped tetra-aniline as a model system, the results and strategies presented in this article provide insight into the general scheme of shape and size control for organic materials.

Capacitors as energy storage device have well-known advantages versus electrochemical energy storage, e.g. a battery. Compared to batteries, capacitors are able to store energy with very high power density, i.e. charge/recharge rates, have long shelf life with little degradation, and can be charged and discharged (cycled) hundreds of thousands or millions of times.

However, capacitors often do not store energy in such little volume or weight as in a battery, or at low cost per energy stored, making capacitors impractical for applications such as in electric vehicles. Accordingly, it would be an advance in energy storage technology to provide storing energy more densely per volume and/or mass.

Aspects of the present disclosure provide solutions to the problem of the further increase of volumetric and mass density of reserved energy of the energy storage device, and at the same time reduces cost of materials and manufacturing process.

SUMMARY

The present disclosure provides an energy storage molecular material, crystal dielectric layer and capacitor which may solve a problem of the further increase of volumetric and mass density of reserved energy associated with some energy storage devices, and at the same time reduce cost of materials. The energy storage molecular material is a relatively low molecular weight dielectric crystalline material having a molecular structure. Other dielectric materials, e.g. and polymers are also molecular but are characterized by a distribution of molecular weight.

In an aspect, the present disclosure provides an energy storage molecular material having a general molecular structural formula:

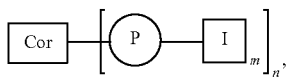

where Cor is a predominantly planar polycyclic molecular system which forms column-like supramolecular stacks by means of π-π-interaction, P is a polarization unit providing polarization, I is a high-breakdown insulating substituent group, n is 1, 2, 3, 4, 5, 6, 7 or 8, m is 1, 2, 3, 4, 5, 6, 7 or 8.

In another aspect, the present disclosure provides an energy storage molecular material having a general molecular structural formula:

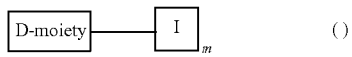

wherein D-moiety is a polarization unit forming column-like supramolecular stacks by means of π-π-interaction, I is a high-breakdown insulating substituent group, m is 1, 2, 3, 4, 5, 6, 7 or 8.

In yet another aspect, the present disclosure provides a crystal dielectric layer comprising the disclosed energy storage molecular material.

In still another aspect, the present disclosure provides a capacitor comprising a first electrode, a second electrode, and a crystal dielectric layer disposed between said first and second electrodes. The electrodes are flat and planar and positioned parallel to each other. The crystal dielectric layer comprises the disclosed energy storage molecular material.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1 is a schematic diagram of a capacitor according to an aspect of the present disclosure.

DETAILED DESCRIPTION

While various aspects of the present disclosure have been shown and described herein, it will be obvious to those skilled in the art that such aspects are provided by way of example only. Numerous variations, changes, and substitutions may occur to those skilled in the art without departing from the invention. It should be understood that various alternatives to the aspects of the disclosure described herein may be employed.

The present disclosure provides an energy storage molecular material. According to and aspect of the present disclosure the energy storage molecular material contains three components which carry out different (various) functions. The predominantly planar polycyclic molecular systems (Cors) give to the energy storage molecular material an ability to form supramolecules. In turn supramolecules allow forming crystal structure of the crystal dielectric layer. The polarization units (P) are used for providing the molecular material with high dielectric permeability. There are several types of polarizability such as dipole polarizability, ionic polarizability, and hyper-electronic polarizability of molecules, monomers and polymers possessing metal conductivity. All polarization units with the listed types of polarization may be used in aspects of the present disclosure. The insulating substituent groups (I) provide electric isolation of the supramolecules from each other in the dielectric crystal layer and provide high breakdown voltage of the energy storage molecular material.

According to one aspect of the present disclosure, the planar polycyclic molecular system may comprise tetrapirolic macro-cyclic fragments having a general structural formula from the group comprising structures 1-6 as given in Table 1, where M denotes an atom of metal or two protons (2H).

TABLE 1

Examples of the polycyclic molecular systems comprising tetrapirolic macro-cyclic fragments

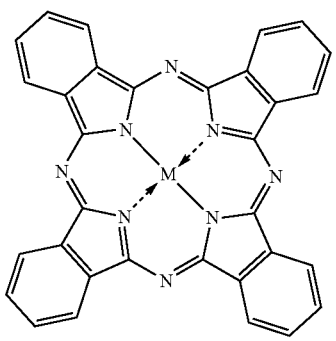

1

TABLE 1-continued

Examples of the polycyclic molecular systems comprising tetrapirolic macro-cyclic fragments

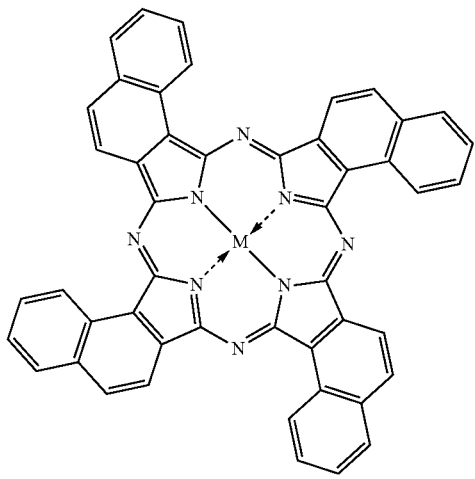

2

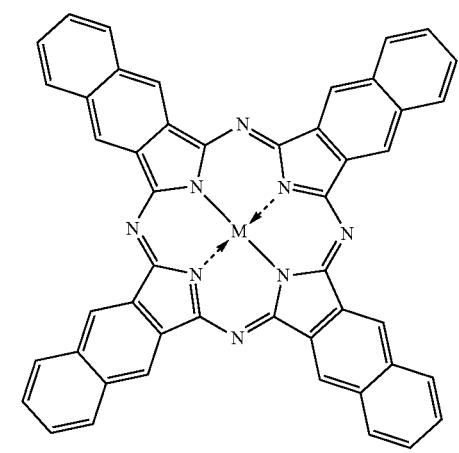

3

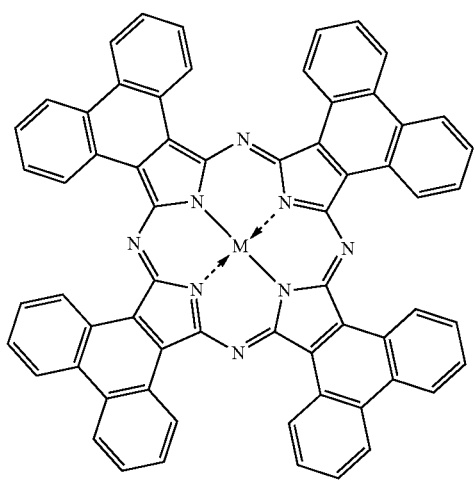

4

TABLE 1-continued

Examples of the polycyclic molecular systems comprising tetrapirolic macro-cyclic fragments

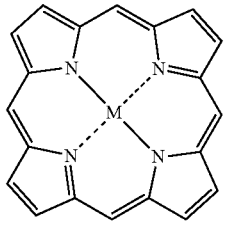

5

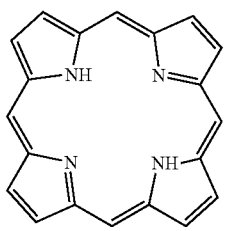 [SMILES: C1=Cc2cc3ccc(cc4nc(cc5ccc(cc1n2)[nH]5)C=C4)[nH]3]

6

According to another aspect of the present disclosure, the planar polycyclic molecular system may comprise planar fused polycyclic hydrocarbons selected from the list comprising truxene, decacyclene, antanthrene, hexabenzotriphenylene, 1.2,3.4,5.6,7.8-tetra-(peri-naphthylene)-anthracene, dibenzoctacene, tetrabenzoheptacene, peropyrene, hexabenzocoronene and has a general structural formula from the group comprising structures 7-17 as given in Table 2.

TABLE 2

Examples of the polycyclic molecular systems comprising planar fused polycyclic hydrocarbons

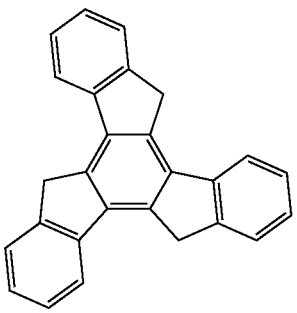 [SMILES: c1ccc2c(c1)Cc1c-2c2c(c3c1-c1ccccc1C3)-c1ccccc1C2]

7

8

TABLE 2-continued

Examples of the polycyclic molecular systems comprising planar fused polycyclic hydrocarbons

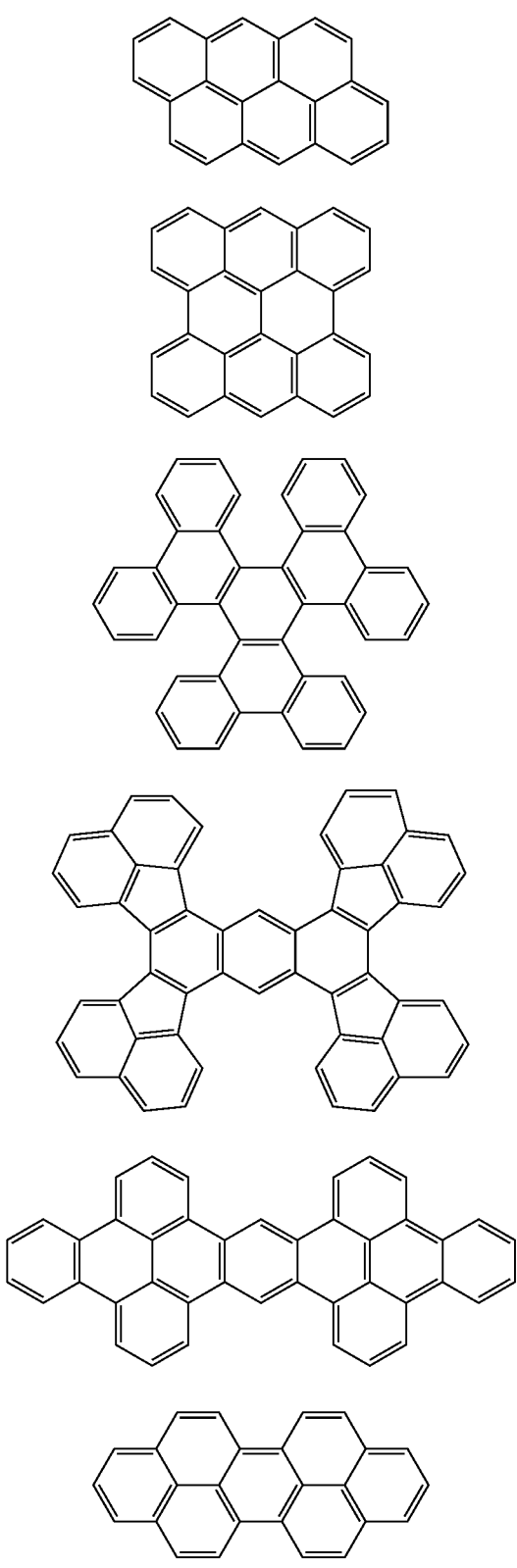

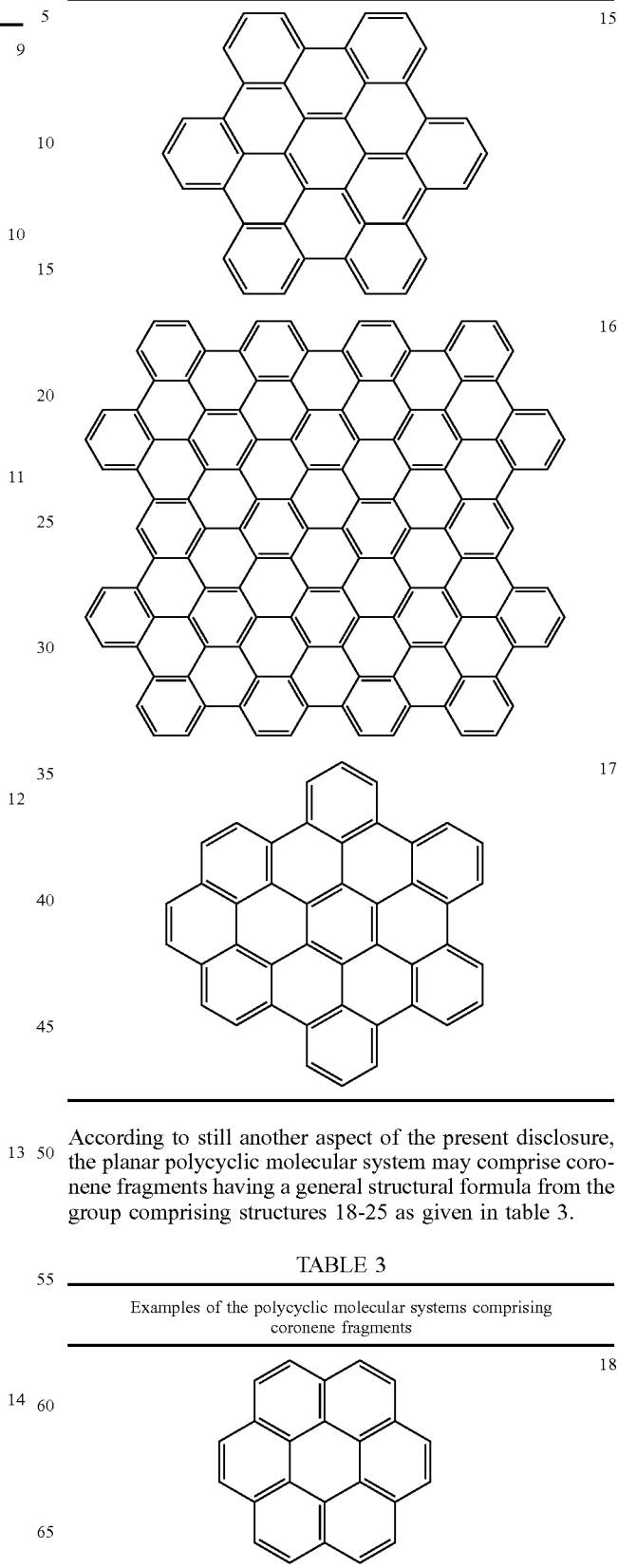

According to still another aspect of the present disclosure, the planar polycyclic molecular system may comprise coronene fragments having a general structural formula from the group comprising structures 18-25 as given in table 3.

TABLE 3

Examples of the polycyclic molecular systems comprising coronene fragments

TABLE 3-continued

Examples of the polycyclic molecular systems comprising coronene fragments

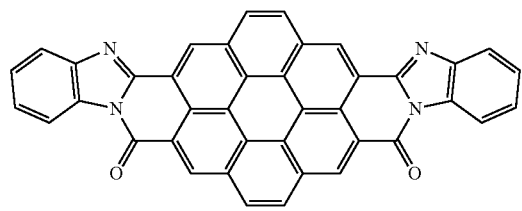 [SMILES: O=c1c2cc3ccc4cc5c(=O)n6c7ccccc7nc6c6cc7ccc8cc(c2c2c3c4c(c56)c7c82)c2nc3ccccc3n12]

19

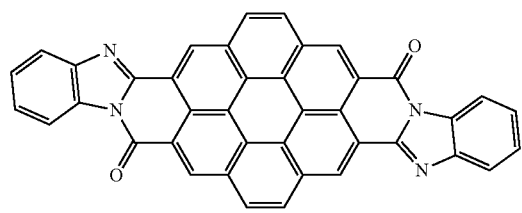 [SMILES: O=c1c2cc3ccc4cc5c6c(cc7ccc8cc(c2c2c3c4c6c7c82)c2nc3ccccc3n12)c(=O)n1c2ccccc2nc51]

20

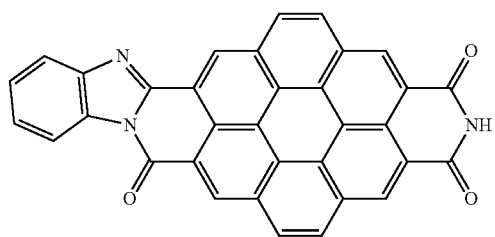 [SMILES: O=C1NC(=O)c2cc3ccc4cc5c6c(cc7ccc8cc1c2c1c8c7c6c4c31)c(=O)n1c2ccccc2nc51]

21

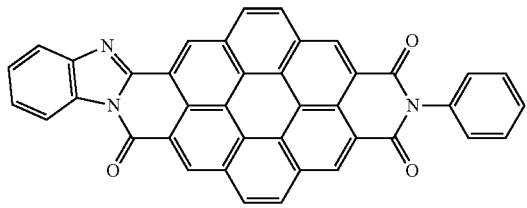 [SMILES: O=C1c2cc3ccc4cc5c(=O)n6c7ccccc7nc6c6cc7ccc8cc(c2c2c3c4c(c56)c7c82)C(=O)N1c1ccccc1]

22

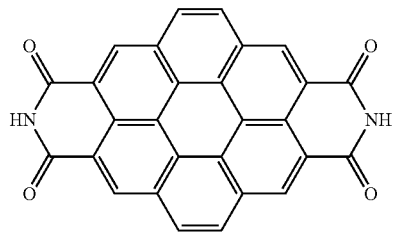 [SMILES: O=c1[nH]c(=O)c2cc3ccc4cc5c(=O)[nH]c(=O)c6cc7ccc8cc1c2c1c8c7c(c65)c4c31]

23

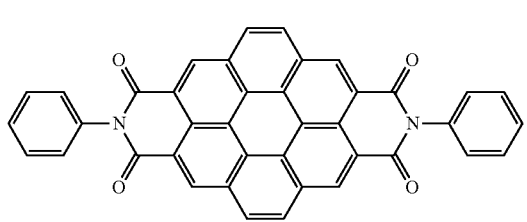 [SMILES: O=c1c2cc3ccc4cc5c(=O)n(-c6ccccc6)c(=O)c6cc7ccc8cc(c(=O)n1-c1ccccc1)c2c1c3c4c(c56)c7c81]

24

TABLE 3-continued

Examples of the polycyclic molecular systems comprising coronene fragments

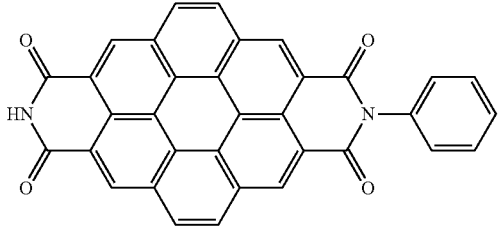 [SMILES: O=c1[nH]c(=O)c2cc3ccc4cc5c(=O)n(-c6ccccc6)c(=O)c6cc7ccc8cc1c2c1c8c7c(c65)c4c31]

25

In yet another aspect of the present disclosure, the polarization unit may comprise the electro-conductive oligomer of structures 26 to 32 as given in Table 4 wherein X=2, 3, 4, 5, 6, 7, 8, 9, 10, 11 or 12.

TABLE 4

Examples of the polarization units comprising the electro-conductive oligomer

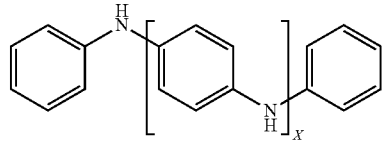

26

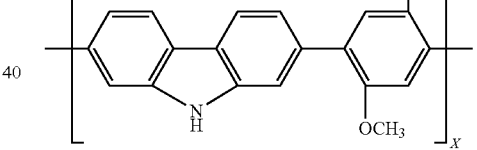

27

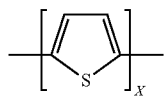

28

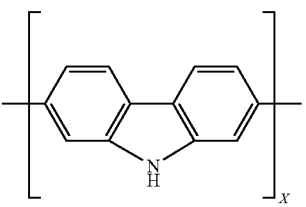

29

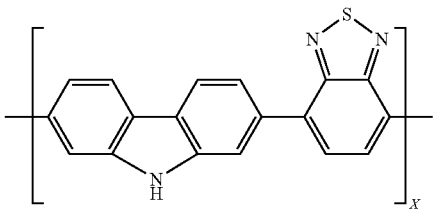

30

TABLE 4-continued

Examples of the polarization units comprising the electro-conductive oligomer

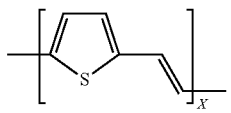 31

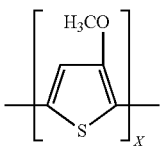 32

In still another aspect of the present disclosure, the polarization unit may comprise rylene fragments having a general structural formula from the group comprising structures 33-53 as given in Table 5.

TABLE 5

Examples of the polarization units comprising the rylene fragments

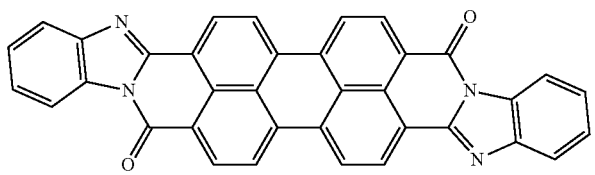 [SMILES: O=c1c2ccc3c4ccc5c6c(ccc(c7ccc(c2c37)c2nc3ccccc3n12)c46)c(=O)n1c2ccccc2nc51] 33

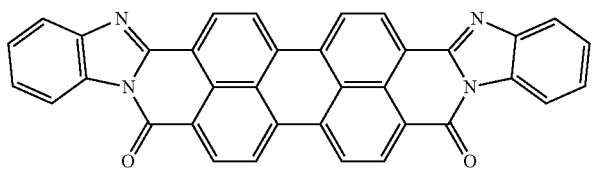 [SMILES: O=c1c2ccc3c4ccc5c(=O)n6c7ccccc7nc6c6ccc(c7ccc(c2c37)c2nc3ccccc3n12)c4c56] 34

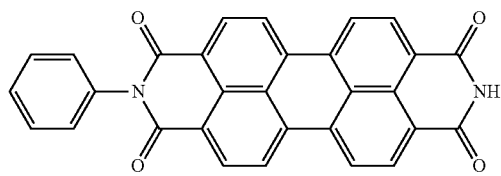 [SMILES: O=C1NC(=O)c2ccc3c4ccc5c6c(ccc(c7ccc1c2c73)c64)C(=O)N(c1ccccc1)C5=O] 35

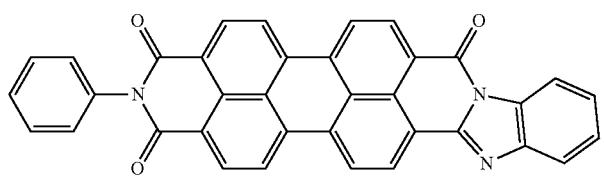 36

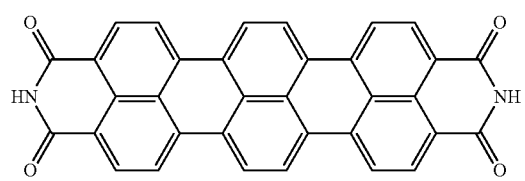 37

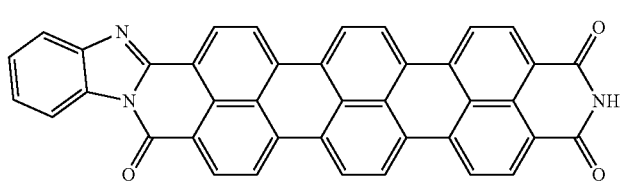 38

TABLE 5-continued
Examples of the polarization units comprising the rylene fragments
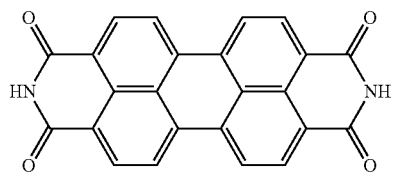 39
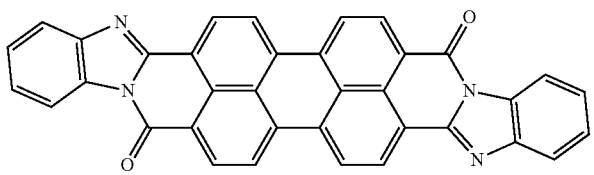 40
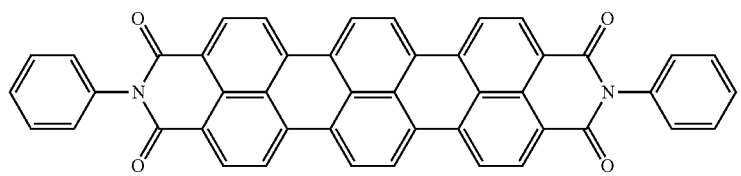 41
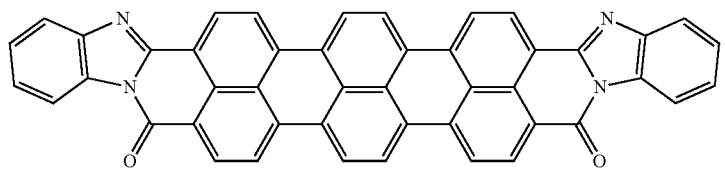 42
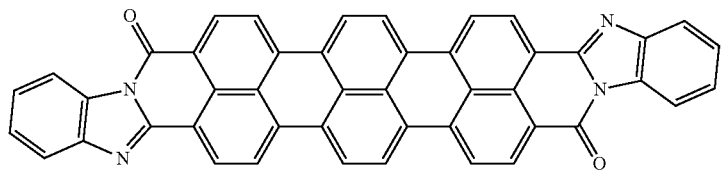 43
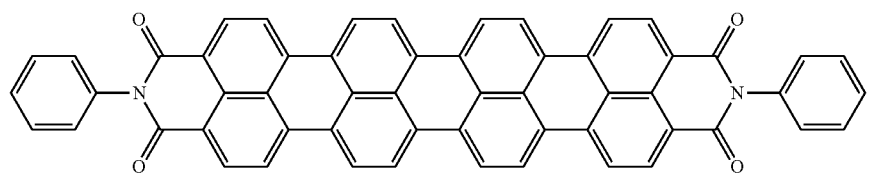 44
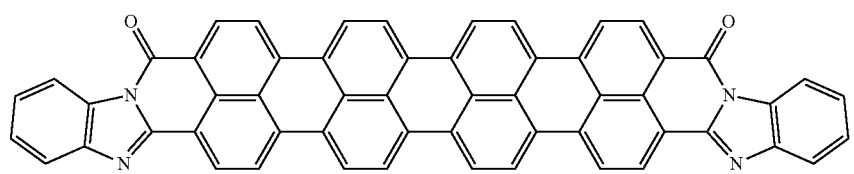 45
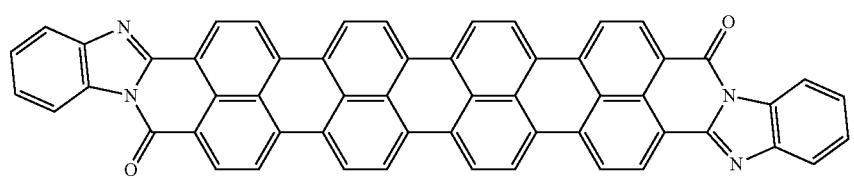 46

TABLE 5-continued

Examples of the polarization units comprising the rylene fragments

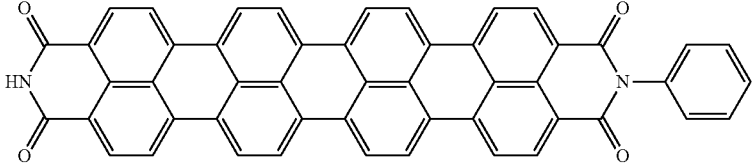

47

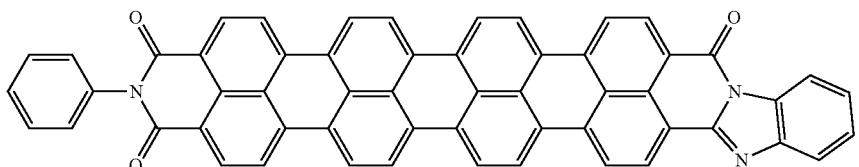

48

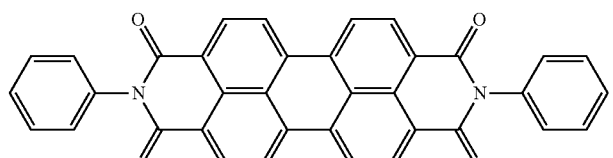

49

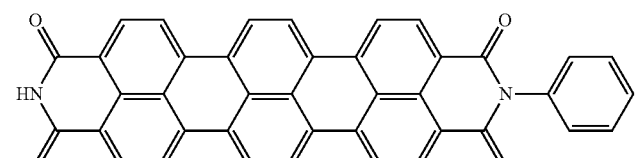

50

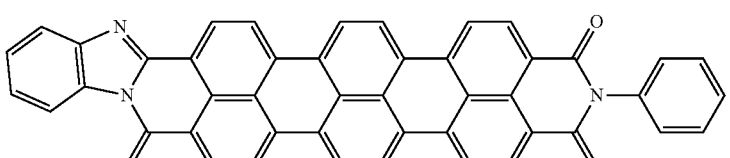

51

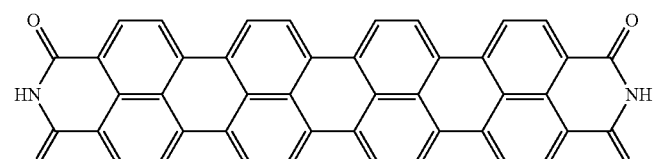

52

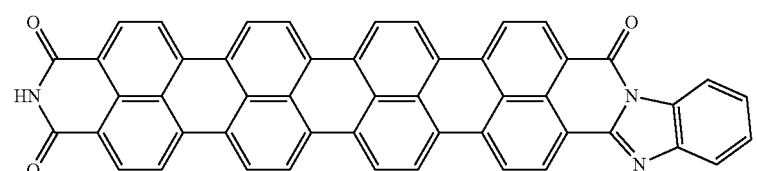

53

According to one aspect of the present disclosure, the polarization unit may be selected from the list comprising doped oligoaniline and p-oligo-phenylene. In another embodiment of the present invention, the doped oligoaniline is self-doped oligoaniline with $SO_3-$ groups or COO— groups on the phenyl rings of aniline. In still another embodiment of the present invention, the doped oligoaniline is mix-doped by acid compounds selected from the list comprising alkyl-$SO_3H$ acid or alkyl-COOH mixed to oligoaniline in oxidized state.

In yet another aspect of the present disclosure, at least one of the high-breakdown insulating substituent group may be independently selected from the list comprising —$(CH_2)_n$—$CH_3$, —$CH((CH_2)_nCH_3)_2$) (where n=1 . . . 50), alkyl, aryl, substituted alkyl, substituted aryl, branched alkyl, branched aryl, and any combination thereof and wherein the alkyl group is selected from methyl, ethyl, propyl, butyl, I-butyl and t-butyl groups, and the aryl group is selected from phenyl, benzyl and naphthyl groups.

In another aspect of the present disclosure the energy storage molecular material may further comprise at least one linker unit selected from the list comprising the following structures: 54-63 as given in Table 6, which connect the predominantly planar polycyclic molecular system (Cor) with the polarization units (P).

TABLE 6

Examples of the linker units

| | |
|---|---|
| —O— | 54 |
| —N(H)— | 55 |
| —O–C(=O)– | 56 |
| —N(H)–C(=O)– | 57 |
| –C(=O)–O— | 58 |
| –C(=O)–N(H)– | 59 |
| –C(CH$_3$)$_2$– | 60 |
| –S(=O)(CH$_3$)– | 61 |
| –S(=O)$_2$–O— | 62 |
| –S(=O)$_2$–N(H)– | 63 |

According to another aspect of the present disclosure, the predominantly planar polycyclic molecular system (Cor) is perylene comprising the polarization units (P) connected to bay positions of perylene structure by linker units (L) where s is equal to 0, 1, 2, 3, 4, 5, or 6:

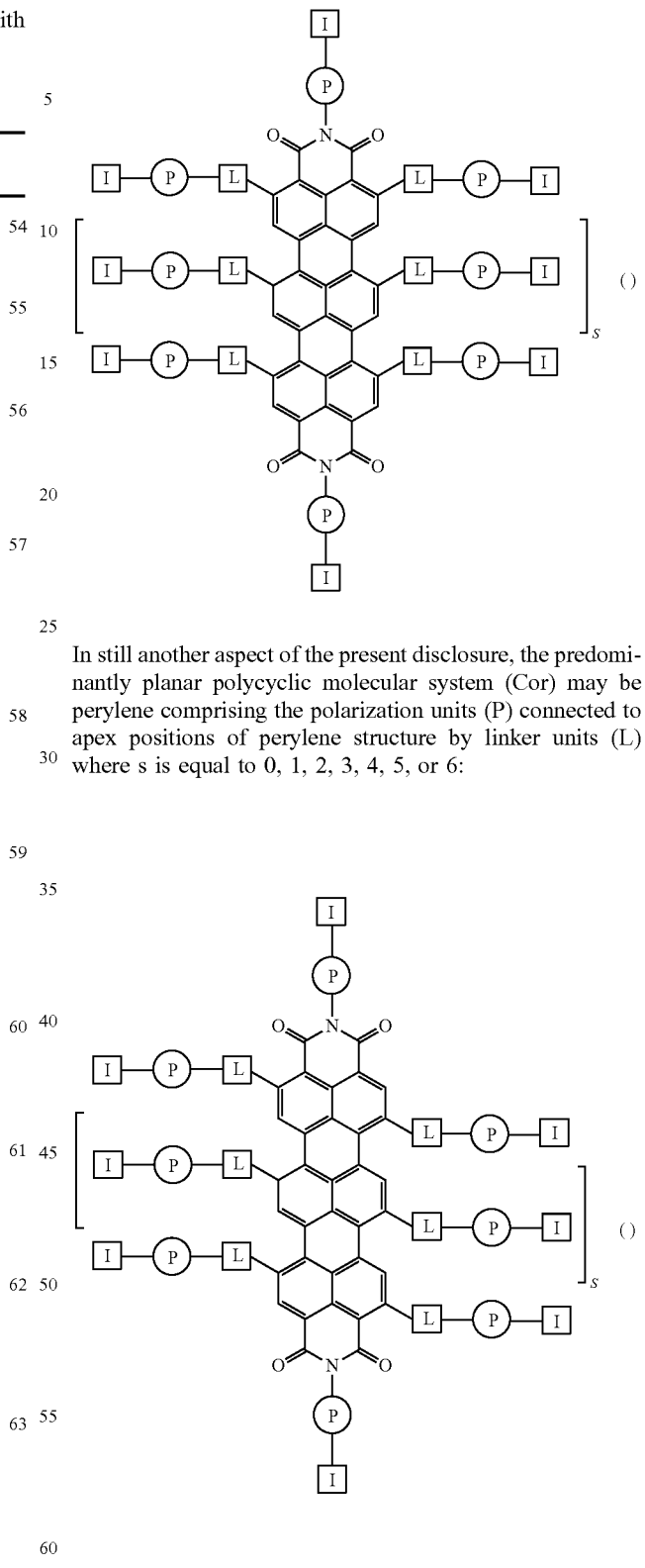

In still another aspect of the present disclosure, the predominantly planar polycyclic molecular system (Cor) may be perylene comprising the polarization units (P) connected to apex positions of perylene structure by linker units (L) where s is equal to 0, 1, 2, 3, 4, 5, or 6:

In yet another aspect of the present disclosure, the predominantly planar polycyclic molecular system (Cor) may be perylene of structural formula where P are the polarization units, I are the high-breakdown insulating substituent groups:

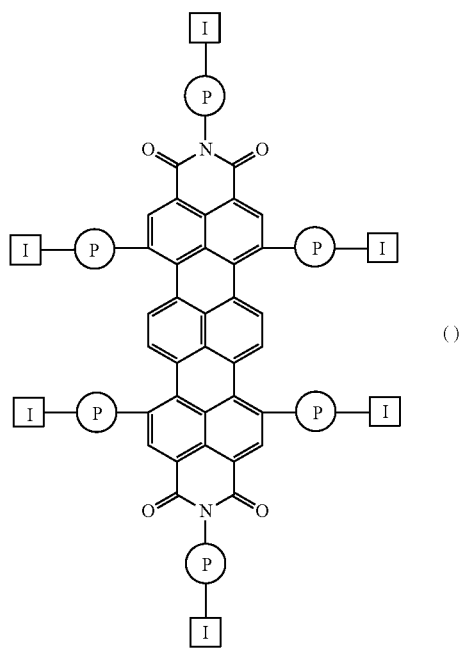

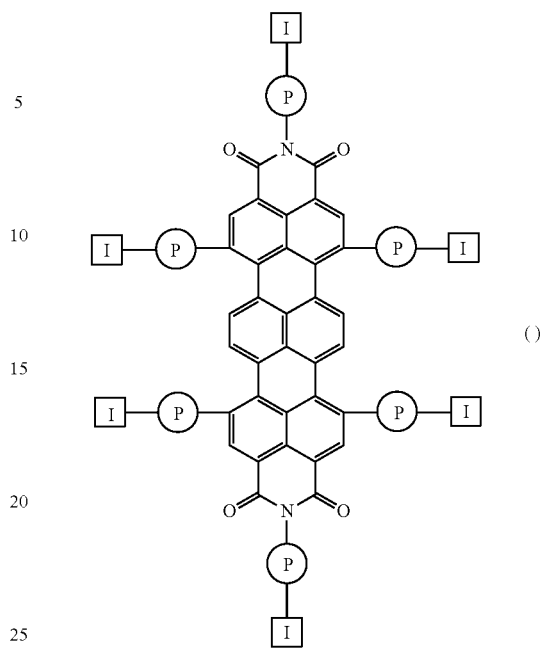

()

In still another aspect of the present disclosure, the predominantly planar polycyclic molecular system (Cor) may be perylene of structural formula:

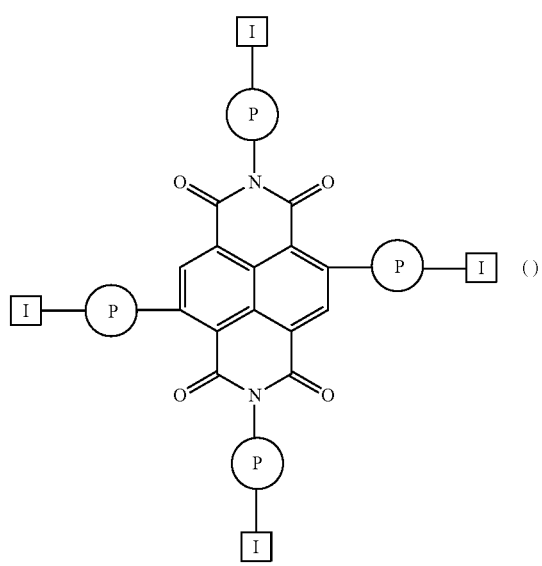

()

where P are the polarization units, I are the high-breakdown insulating substituent groups.

In one aspect of the present disclosure, the predominantly planar polycyclic molecular system (Cor) may be perylene of structural formula:

where P are the polarization units, I are the high-breakdown insulating substituent groups.

Aspects of the present disclosure also include an energy storage molecular material having a general molecular structural formula:

$$\boxed{\text{D-moiety}} \boxed{\phantom{---}\text{I}\phantom{---}}_m \quad ()$$

wherein D-moiety is a polarization unit forming column-like supramolecular stacks by means of π-π-interaction, I is a high-breakdown insulating substituent group, m is 1, 2, 3, 4, 5, 6, 7 or 8. Thus the energy storage molecular material contains two components which carry out different (various) functions. The D-moiety gives to the energy storage molecular material an ability to form supramolecules. In turn supramolecules allow forming crystal structure of the crystal dielectric layer. Also the D-moiety is used for providing the molecular material with high dielectric permeability. There are several types of polarizability such as dipole polarizability, ionic polarizability, and hyper-electronic polarizability of molecules, monomers and polymers possessing metal conductivity. All D-moieties with the listed types of polarization may be used in the present invention. The insulating substituent groups (I) provide electric isolation of the supramolecules from each other in the dielectric crystal layer and provide high breakdown voltage of the energy storage molecular material.

In one aspect of the present disclosure, the D-moiety comprises the electro-conductive oligomer of structures 64 to 70 as given in Table 7 wherein X=2, 3, 4, 5, 6, 7, 8, 9, 10, 11 or 12.

TABLE 7

Examples of the D- moiety comprising electro-conductive oligomers

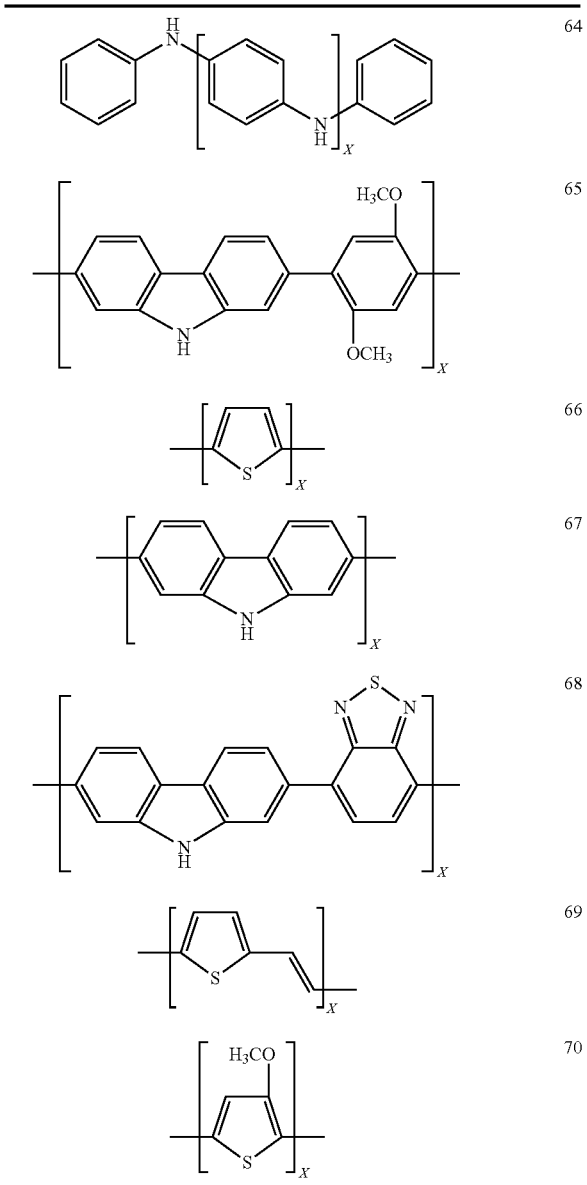

In another aspect of the present disclosure, the D-moiety may be selected from the list comprising doped oligoaniline and p-oligo-phenylene. In still another embodiment of the present invention, the doped oligoaniline is self-doped oligoaniline with SO3-groups or COO-groups on the phenyl rings of aniline. In yet another embodiment of the present invention, the doped oligoaniline is mix-doped by acid compounds selected from the list comprising alkyl-SO$_3$H acid or alkyl-COOH mixed to oligoaniline in oxidized state. In one embodiment of the present invention, at least one of the high-breakdown insulating substituent group (I) is independently selected from the list comprising —(CH$_2$)$_n$—CH$_3$, —CH((CH$_2$)$_n$CH$_3$)$_2$) (where n=1 . . . 50), alkyl, aryl, substituted alkyl, substituted aryl, branched alkyl, branched aryl, and any combination thereof and wherein the alkyl group is selected from methyl, ethyl, propyl, butyl, I-butyl and t-butyl groups, and the aryl group is selected from phenyl, benzyl and naphthyl groups. In another embodiment of the present invention the energy storage molecular material further comprises at least one linker unit presented in structures 71-80 as given in Table 8, which connect the polarization units (D-moiety) with the high-breakdown insulating substituent group.

TABLE 8

Examples of the linker units

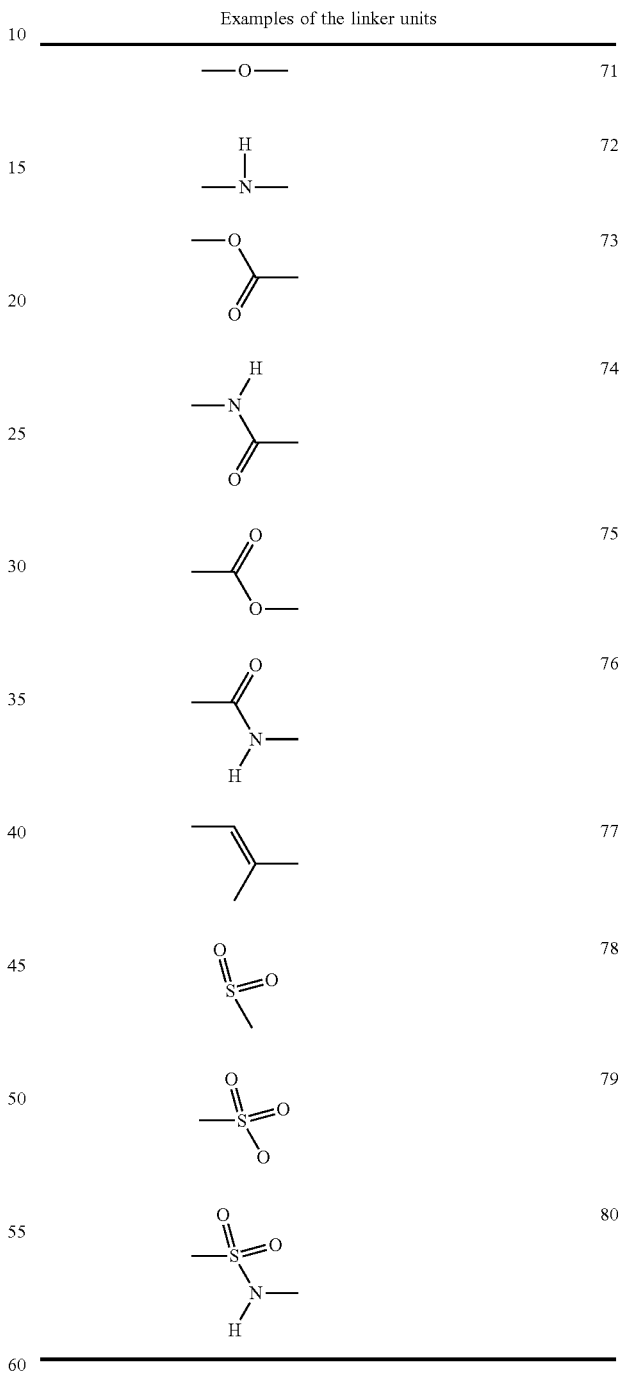

In still another aspect of the present disclosure, the energy storage molecular material may comprise perylene as the D-moiety and the high-breakdown insulating substituent groups (I) may be connected to bay positions of perylene structure by linker units (L) where s is equal to 0, 1, 2, 3, 4, 5, and 6:

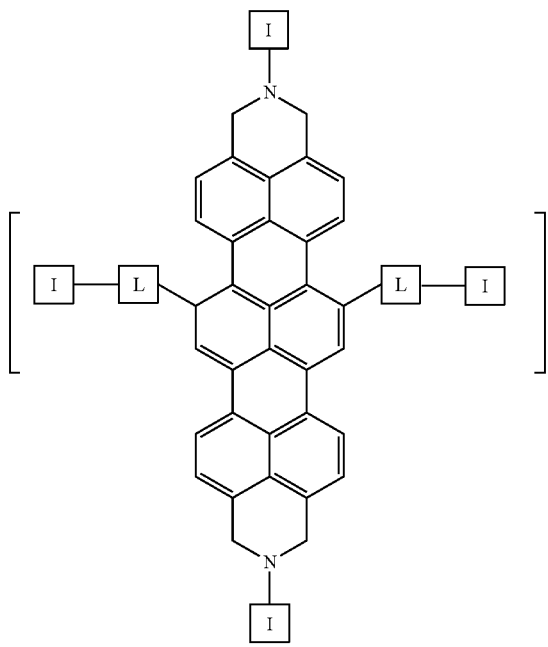

In still another aspect of the present disclosure, the energy storage molecular material may comprise perylene as the D-moiety and the high-breakdown insulating substituent groups (I) may be connected to apex positions of perylene structure by linker units (L) where s is equal to 0, 1, 2, 3, 4, 5, and 6:

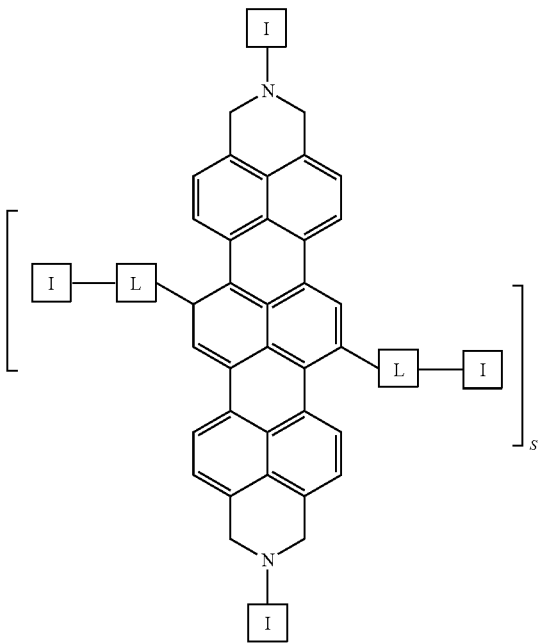

In one aspect of the present disclosure, the energy storage molecular material may have the general structural formula, where m is 1:

According to a related aspect of the present disclosure, the energy storage molecular material may have the general structural formula, where m is 2:

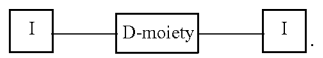

Aspects of the present disclosure include a crystal dielectric layer comprising the disclosed energy storage molecular material. When dissolved in an appropriate solvent, such energy storage molecular material forms a colloidal system (lyotropic liquid crystal) in which molecules are aggregated into supramolecular complexes constituting kinetic units of the system. This lyotropic liquid crystal phase is essentially a precursor of the ordered state of the system, from which the crystal dielectric layer is formed during the subsequent alignment of the supramolecular complexes and removal of the solvent.

By way of example, and not by way of limitation, a method for making the crystal dielectric layers from a colloidal system with supramolecular complexes may include the following steps:

application of the colloidal system onto a substrate. The colloidal system typically possesses thixotropic properties, which are provided by maintaining a preset temperature and a certain concentration of the dispersed phase;

external alignment upon the system, which can be produced using mechanical factors or by any other means, for example by applying an external electric field at normal or elevated temperature, with or without additional illumination, magnetic field, or optical field (e.g., coherent photovoltaic effect); the degree of the external alignment should be sufficient to impart necessary orientation to the kinetic units of the colloidal system and form a structure, which serves as a base of the crystal lattice of the crystal dielectric layer; and drying to remove solvents to form the final crystal dielectric layer structure.

In the resulting crystal dielectric layer, the molecular planes of the predominantly planar polycyclic molecular system are parallel to each other and the energy storage molecular material forms a three-dimensional crystal structure, at least in part of the crystal. Optimization of the production technology may allow the formation of the single crystal dielectric layer.

As seen in FIG. 1, aspects of the present disclosure include a capacitor 100 comprising a first electrode 102, a second electrode 104, and a crystal dielectric layer 106 disposed between said first and second electrodes. The crystal dielectric layer 106 comprises the disclosed energy storage molecular material having a general molecular structural formula:

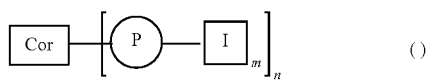

or any of the disclosed variations thereon as discussed herein or a general molecular structural formula:

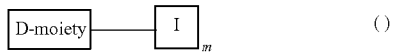 ()

or any of the disclosed variations thereon as discussed herein.

Such materials may be characterized by a dielectric constant κ between about 100 and about 1,000,000 and a breakdown field $E_{bd}$ between about 0.01 V/m and about 2.0 V/nm.

The electrodes may be made of any suitable conductive material, e.g., metals, such as Aluminum (Al) or copper (Cu). In some implementations, one or both electrodes may be made of a foamed metal, such as foamed Aluminum. The electrodes 102, 104 may be flat and planar and positioned parallel to each other. Alternatively, the electrodes may be planar and parallel, but not necessarily flat, e.g., they may coiled, rolled, bent, folded, or otherwise shaped to reduce the overall form fact of the capacitor. It is also possible for the electrodes to be non-flat, non-planar, or non-parallel or some combination of two or more of these. By way of example and not by way of limitation, a spacing d between the electrodes 102, 104, which may correspond to the thickness of the crystal dielectric layer 106 may range from about 1 μm to about 10 000 μm. As noted in Equation (2) above, the maximum voltage $V_{bd}$ between the electrodes 102, 103 is approximately the product of the breakdown field and the electrode spacing d. For example, if, $E_{bd}$=0.1 V/nm and the spacing d is 10,000 microns (100,000 nm), the maximum voltage $V_{bd}$ would be 100,000 volts.

The electrodes may have the same shape as each other, the same dimensions, and the same area A. By way of example, and not by way of limitation, the area A of each electrode 102, 104 may range from about 0.01 m² to about 1000 m². By way of example, and not by way of limitation, for rolled capacitors, electrodes up to, e.g., 1000 m long and 1 m wide are manufacturable with roll-to-roll processes similar to those used to manufacture magnetic tape or photographic film.

These ranges are non-limiting. Other ranges of the electrode spacing d and area A are within the scope of the aspects of the present disclosure.

If the spacing d is small compared to the characteristic linear dimensions of electrodes (e.g., length and/or width), the capacitance C of the capacitor 100 may be approximated by the formula:

$$C=\kappa\varepsilon_o A/d, \quad (3)$$

where $\varepsilon_o$ is the permittivity of free space (8.85×10⁻¹² Coulombs²/(Newton·meter²)) and κ is the dielectric constant of the crystal dielectric layer 106. The energy storage capacity U of the capacitor 100 may be approximated as:

$$U=\tfrac{1}{2}CV_{bd}^2 \quad (4)$$

which may be rewritten using equations (2) and (3) as:

$$U=\tfrac{1}{2}\kappa\varepsilon_o AE_{bd}^2 d \quad (5)$$

The energy storage capacity U is determined by the dielectric constant κ, the area A, and the breakdown field $E_{bd}$. By appropriate engineering, a capacitor or capacitor bank may be designed to have any desired energy storage capacity U. By way of example, and not by way of limitation, given the above ranges for the dielectric constant κ, electrode area A, and breakdown field $E_{bd}$ a capacitor in accordance with aspects of the present disclosure may have an energy storage capacity U ranging from about 500 Joules to about 2×10¹⁶ Joules.

For a dielectric constant κ ranging, e.g., from about 100 to about 1,000,000 and constant breakdown field $E_{bd}$ between, e.g., about 0.1 and 0.5 V/nm, a capacitor of the type described herein may have a specific energy capacity per unit mass ranging from about 10 W·h/kg up to about 100,000 W·h/kg, though implementations are not so limited.

In order that aspects of the present disclosure may be more readily understood, reference is made to the following examples, which are intended to be illustrative of the invention, but are not intended to be limiting the scope.

Example 1

The example describes a method of synthesis of porphyrin-(phenyl-perylene diimide)₄-compound (TPP-PDI₄) represented by the general structural formula I and comprising fragments represented by structural formulas 6 and 35 (Tables 1 and 5),

I

-continued

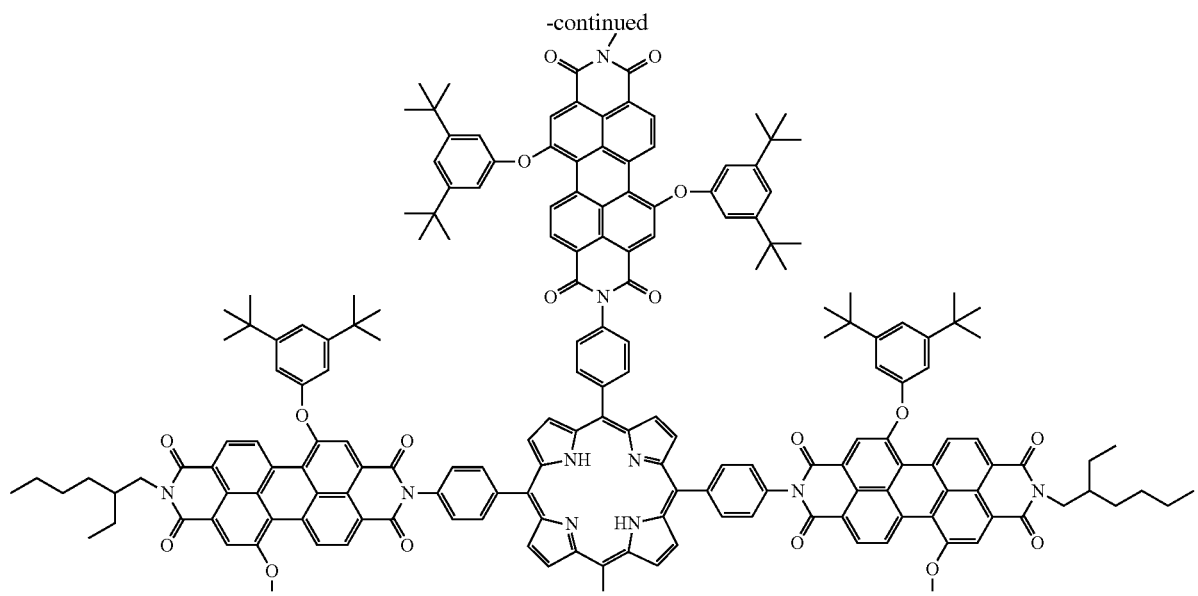

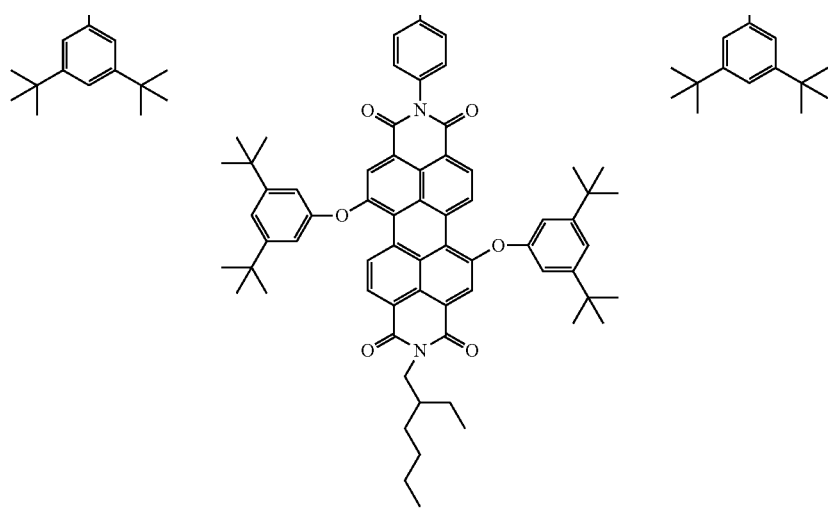

TPP-PDI₄

The method comprises several steps.

In the first step a synthesis of 1,7-dibromoperylene-3,4:9,10-tetracarboxydianhydride represented by the general structural formula 81 was carried out:

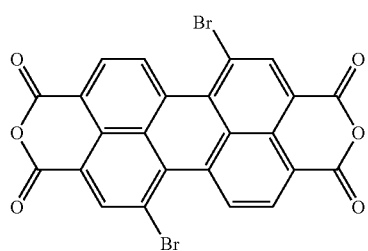

For this purpose 3,4:9,10-perylenetetracarboxylic dianhydride (28.52 g, 72.7 mmol) was added to 420 ml concentrated sulfuric acid and stirred at 55° C. for 24 hours. Iodine (0.685 g, 2.70 mmol) was added to the reaction mixture and stirred for additional 5 hours. at 55° C. Bromine (8.3 ml, 162 mmol) was added dropwise to the reaction flask over 1 hour and stirred for 24 hours at 85° C. The excess bromine was then displaced with the nitrogen gas $N_2$. Water (66 ml) was added dropwise to the cooled mixture and the precipitate was filtered off. The crude product was washed with 220 ml 86% $H_2SO_4$ followed by water and this procedure was repeated two times to produce the crude product (32.32 g, 81%). This product was used further without any purification. M.S.: 549.0 (calcd. 550.11).

In the second step a synthesis of 1,7-(3',5'-di-t-butylphenoxy)perylene-3,4:9,10-tetracarboxydianhydride (PDA) represented by the general structural formula 82 was carried out.

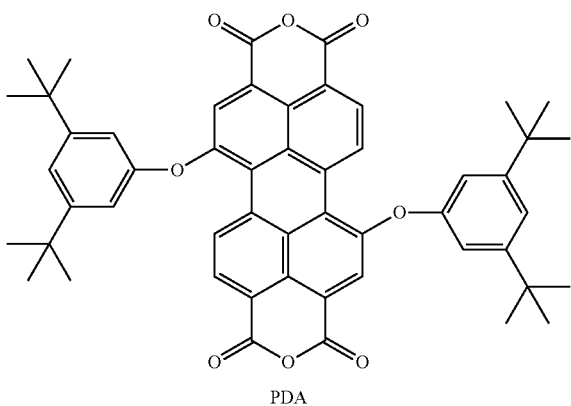

PDA

For this purpose 1,7-Dibromoperylene-3,4,9,10-tetracarboxydianhydride (0.89 g, 1.61 mmol), 3,5-di-tert-butylphenol (1.0 g, 4.85 mmol), and $Cs_2CO_3$ (1.1 g, 3.38 mmol) were placed into two-neck flask equipped with magnetic stirrer bar, air condenser, and argon outlet. Then DMF (15 mL) was added and the resulting suspension was refluxed with the intensive stirring for 1.5 hours. An initially red suspension turned to a deep violet one. Reaction mixture was cooled to room temperature and acetic acid (10 mL) was added. The formed precipitate was stirred overnight at room temperature, filtered off, washed with ice cold acetic acid (40 mL) and hot MeOH (40 mL), dried under vacuum for 6 hours at 60° C. to give pure product 1.2 g (87%). M.S.: 799.9 (calcd. 800.3). $^1H$ NMR ($CDCl_3$) δ: 9.69 (d, J=8.4, Hz, 2H), 8.68 (d, J=8.4 Hz, 2H), 8.37 (s, 2H), 7.42 (t, J=1.7, 2H), 7.03 (d, J=1.7, 4H), 1.35 (s, 36H).

In the third step a synthesis of N-(2-ethylhexyl)-1,7-(3',5'-di-t-butylphenoxy)perylene-3,4-dicarboxyanhydride-9,10-dicarboximide (PIA) represented by the general structural formula 83 was carried out:

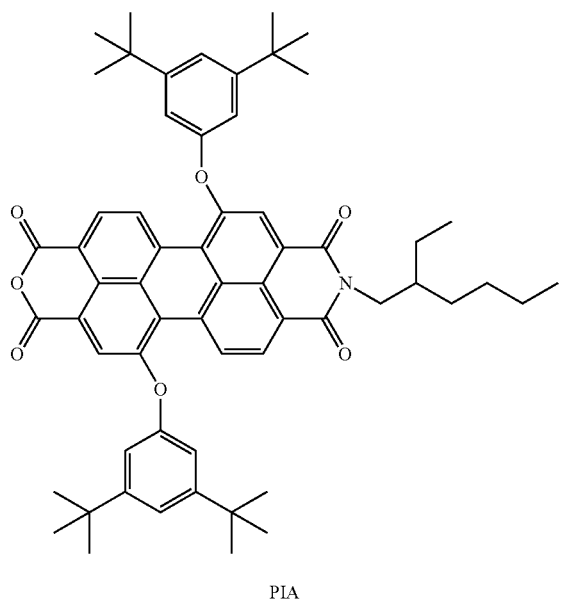

PIA

For this purpose 1,7-(3'5'-Di-t-butylphenoxy)perylene-3,4,9,10-tetracarboxydianhydride (PDA) (0.85 g, 1.06 mmol), imidazole (0.85 g, 12.4 mmol) were placed into a three-neck flask equipped with magnetic stirrer bar, air condenser, argon inlet tube, and dropping funnel. Chloroform (250 mL, freshly distilled from $CaH_2$) was added. The resulting suspension was refluxed with the intensive stirring for 1 hour and 2-ethylhexylamine (0.136 g, 1.06 mmol) in chloroform (8 mL) was added dropwise for 1 hour, followed by 5 drops of $CF_3COOH$. Reaction mixture was refluxed for 3 days, cooled down, the solvent was removed under reduced vacuum. The product was purified on column chromatography on silica gel (eluent $CHCl_3$-hexane 4:1) to produce an analytically pure monoanhydride (PIA) as red solid material (Yield: 0.24 g, 24%). M.S.: 911.50 (calcd. 911.48). $^1H$ NMR ($CDCl_3$) δ: 9.70 (d, J=2.6 Hz, 1H), 9.68 (d, J=2.6 Hz, 1H), 8.64 (d, J=5.03 Hz, 1H), 8.62 (d, J=5.03 Hz, 1H), 8.36 (s, 1H), 8.33 (s, 1H), 7.38 (t, J=1.7 Hz, 1H), 7.37 (t, J=1.7 Hz, 1H), 7.027 (d, J=1.7 Hz, 2H), 7.02 (d, J=1.7 Hz, 2H), 4.10 (m, 2H), 1.98 (m, 1H), 1.34 (m, 6H), 1.21 (s, 18H), 1.20 (s, 18H), 0.91 (m, 8H).

In the last step a final assembling of porphyrin-(phenylperylene diimide)$_4$-compound (TPP-PDI$_4$) represented by the general structural formula I was carried out. For this purpose 5,10,15,20-Tetrakis(p-aminophenyl)porphyrin (50 mg, 0.074 mmol), PIA (334 mg, 0.36 mmol) and imidazole (3.0 g) are added to 10 ml of pyridine. The reaction mixture was heated to reflux under dry nitrogen for 2 days with stirring. The reaction is slow (monitored by MALDI) and additional PIA (252 mg, 0.28 mmol) was added. The reaction mixture was refluxed for another 2 days and then diluted with chloroform, washed one time with 2N hydrochloric acid, 2 times with water, dried over anhydrous potassium carbonate, and the solvent stripped on a rotary evaporator. The residue is column chromatographed on silica gel with chloroform to afford TPP-PDI$_4$ (130 mg, 40%). Mass spectrum: 4245 (calc. 4245) $^1H$ NMR δ ($CDCl_3$) 9.8 (broad, 4H), 9.7 (broad 4H), 8.8 (broad, 4H), 8.6 (broad, 4H), 8.5 (broad, 4H), 8.2 (broad, 4H), 7.7 (broad, 4H), 7.5 (broad, 4H), 7.47 (broad, 8H), 7.39 (broad, 8H), 7.15 (broad, 24H), 4.1 (m, 8H), 2.7 (s, 12H), 2.7 (broad, 24H), 2.0 (broad, 4H), 1.3 (broad, 24H), 1.4 (broad, 144H), 0.8 (broad, 32H). The synthesis of TPP-PDI$_4$ have been performed according with known literature procedures (see, 1.) van der Boom, T.; Hayes, R. T.; Zhao, Y.; Bushard, P. J.; Weiss, E. A.; Wasielewski, M. R. *J. Am. Chem. Soc.* 2002, 124, 9582; 2.) M. J. Ahrens, L. E. Sinks, B. Rybtchinski, W. Liu, B. A. Jones, J. M. Giaimo, A. V. Gusev, A. J. Goshe, D. M. Tiede, M. R. Wasielewski, *J. Am. Chem. Soc.*, 2004, 126, 8284).

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "A", or "An" refers to a quantity of one or more of the item following the article, except where expressly stated otherwise. As used herein, in a listing of elements in the alternative, the term "or" is used as the inclusive sense, e.g., "X or Y" covers X alone, Y alone, or both X and Y together, except where expressly stated otherwise. Two or more elements listed as alternatives may be combined together. The appended claims are not to be interpreted as including

What is claimed is:

1. An energy storage molecular material having a general molecular structural formula:

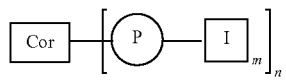

wherein Cor is a predominantly planar polycyclic molecular system which forms column-dike supramolecular stacks by means of π-π-interaction, wherein the planar polycyclic molecular system comprises planar fused polycyclic hydrocarbons selected from the group of truxene, decacyclene, antanthrene, hexabenzotriphenylene, 1,2,3,4,5,6,7,8-tetra-(peri-naphthylene)-anthracene, dibenzoctacene, tetrabenzoheptacene, peropyrene, hexabenzocoronene and has a general structural formula 7-17:

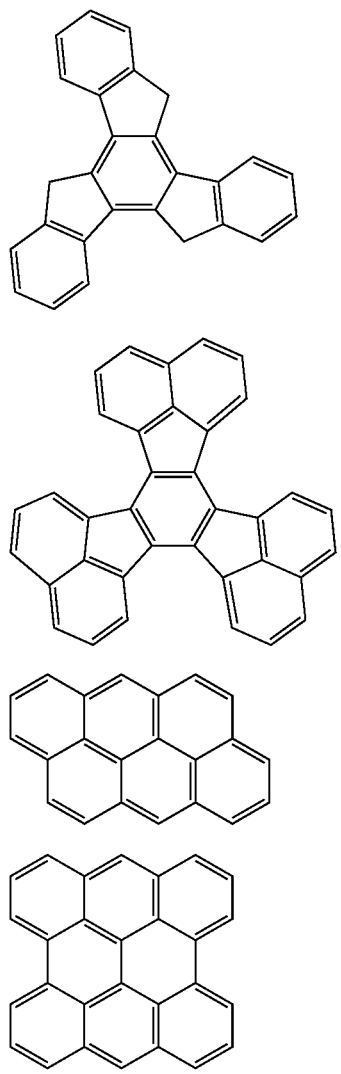

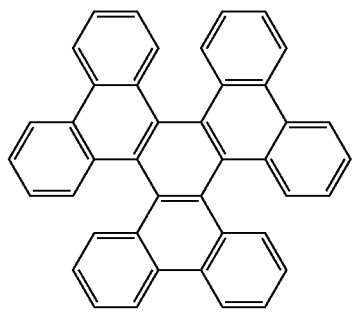

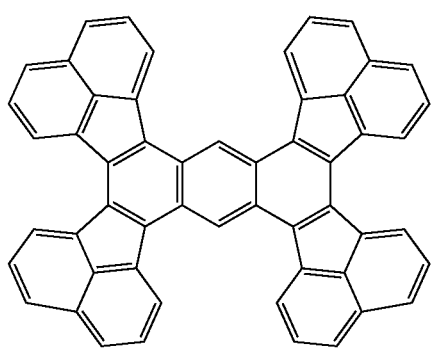

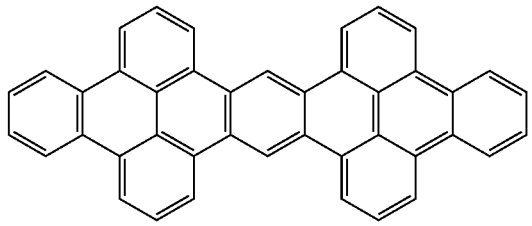

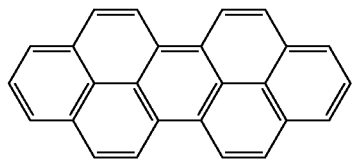

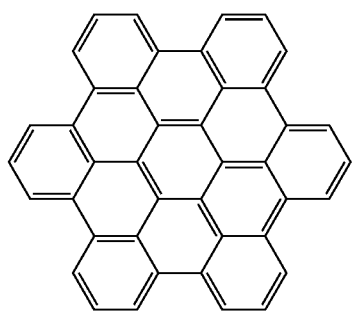

16
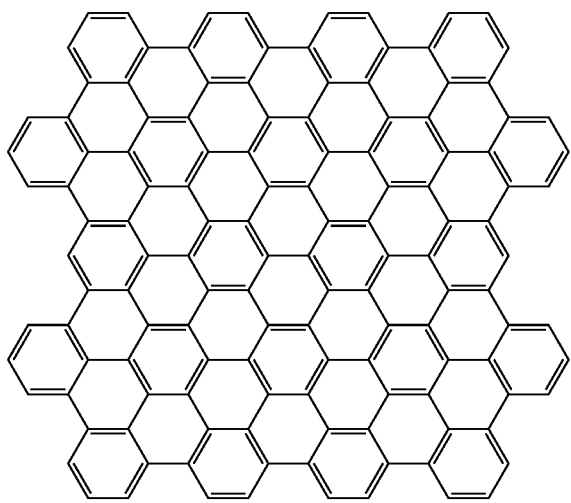
17
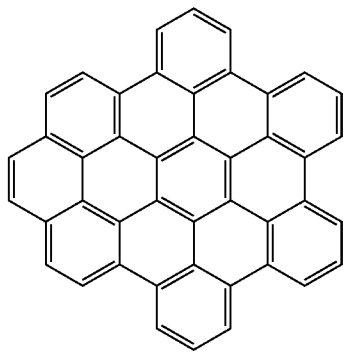
P is a polarization unit, wherein the polarization unit is comprised of rylene fragments of a general structure selected from the group of structures 33-53:
33
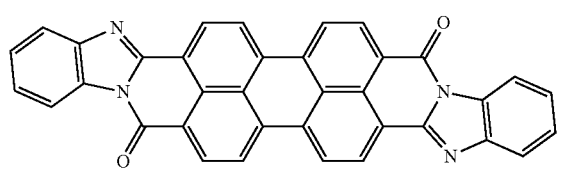
34
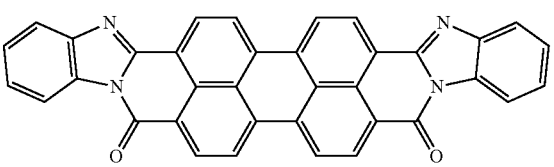
35
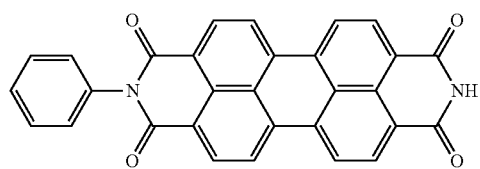
36
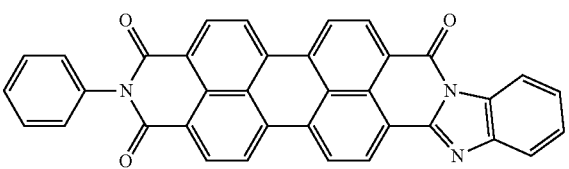 [SMILES: O=C1c2ccc3c4ccc5c(=O)n6c7ccccc7nc6c6ccc(c7ccc(c2c37)C(=O)N1c1ccccc1)c4c56]
37
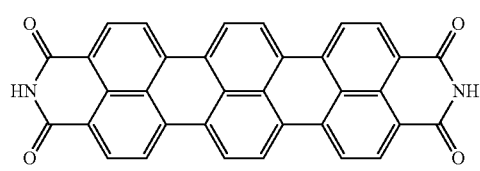 [SMILES: O=C1NC(=O)c2ccc3c4ccc5c6ccc7c8c(ccc(c9ccc(c%10ccc1c2c%103)c4c95)c86)C(=O)NC7=O]
38
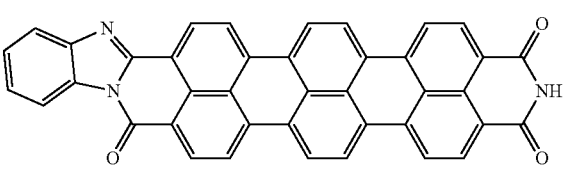
39
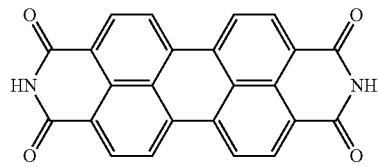 [SMILES: O=C1NC(=O)c2ccc3c4ccc5c6c(ccc(c7ccc1c2c73)c64)C(=O)NC5=O]
40
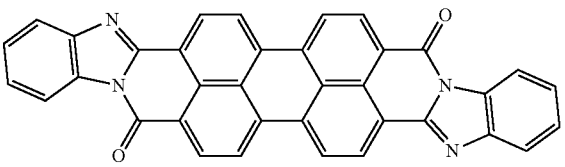 [SMILES: O=c1c2ccc3c4ccc5c6c(ccc(c7ccc(c2c37)c2nc3ccccc3n12)c46)c(=O)n1c2ccccc2nc51]
41
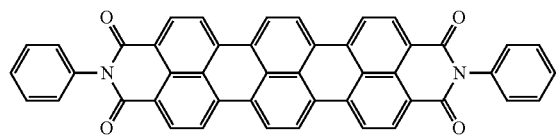
42
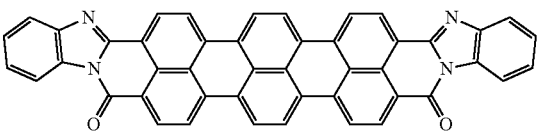

43
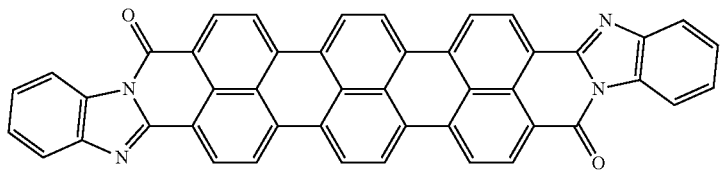 [SMILES: O=c1c2ccc3c4ccc5c6ccc7c8c(ccc(c9ccc(c%10ccc(c2c3%10)c2nc3ccccc3n12)c4c95)c68)c(=O)n1c2ccccc2nc71]
44
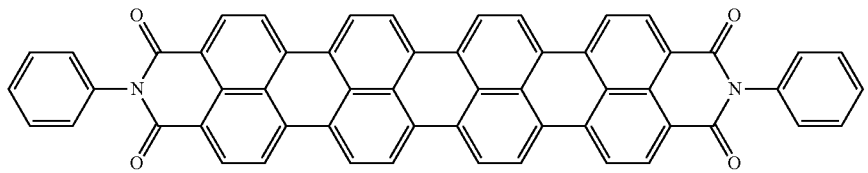 [SMILES: O=C1c2ccc3c4ccc5c6ccc7c8ccc9c%10c(ccc(c%11ccc(c%12ccc(c%13ccc(c2c3%13)C(=O)N1c1ccccc1)c4c5%12)c6c7%11)c%108)C(=O)N(c1ccccc1)C9=O]
45
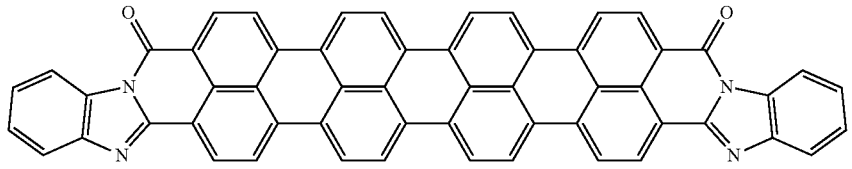
46
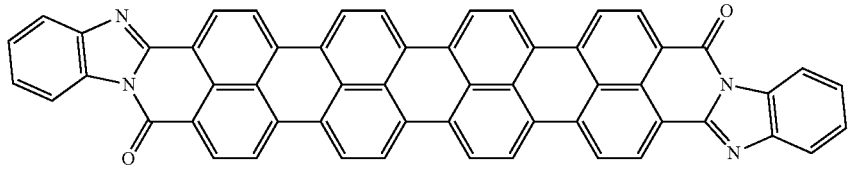 [SMILES: O=c1c2ccc3c4ccc5c6ccc7c8ccc9c%10c(ccc(c%11ccc(c%12ccc(c%13ccc(c2c3%13)c2nc3ccccc3n12)c4c5%12)c6c%117)c8%10)c(=O)n1c2ccccc2nc91]
47
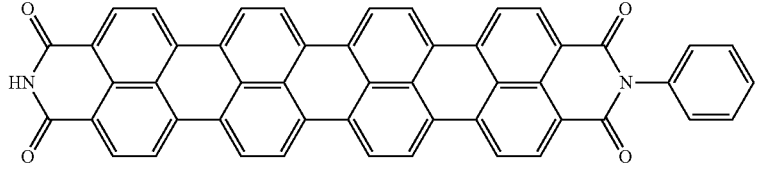 [SMILES: O=C1NC(=O)c2ccc3c4ccc5c6ccc7c8ccc9c%10c(ccc(c%11ccc(c%12ccc(c%13ccc1c2c%133)c4c%125)c6c%117)c%108)C(=O)N(c1ccccc1)C9=O]
48
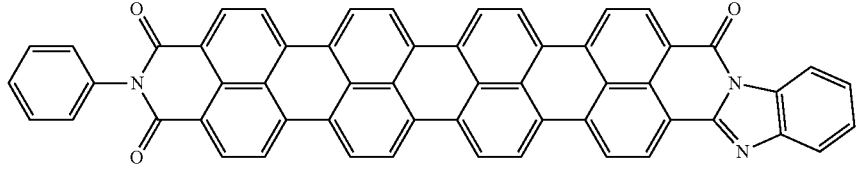 [SMILES: O=C1c2ccc3c4ccc5c6ccc7c8ccc9c(=O)n%10c%11ccccc%11nc%10c%10ccc(c%11ccc(c%12ccc(c%13ccc(c2c3%13)C(=O)N1c1ccccc1)c4c5%12)c6c7%11)c8c9%10]
49
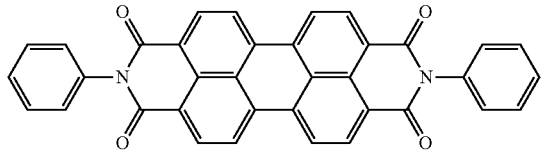 [SMILES: O=C1c2ccc3c4ccc5c6c(ccc(c7ccc(c2c37)C(=O)N1c1ccccc1)c64)C(=O)N(c1ccccc1)C5=O]
50
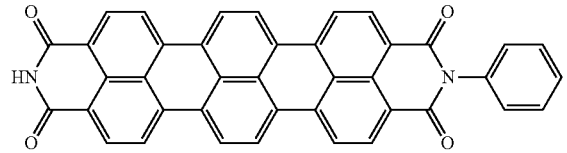
51
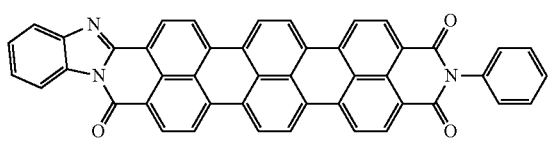
52
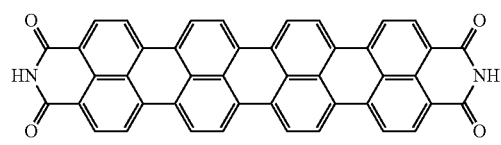
53
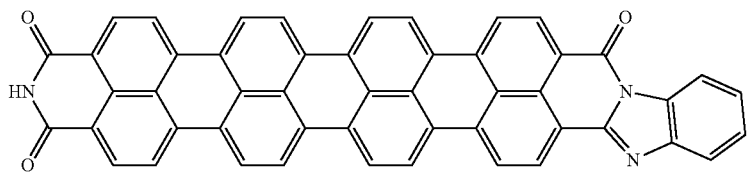 [SMILES: O=C1NC(=O)c2ccc3c4ccc5c6ccc7c8ccc9c%10c(ccc(c%11ccc(c%12ccc(c%13ccc1c2c%133)c4c%125)c6c%117)c8%10)c(=O)n1c2ccccc2nc91]

I is a high-breakdown insulating substituent group,
n is 1, 2, 3, 4, 5, 6, 7 or 8,
m is 1, 2, 3, 4, 5, 6, 7 or 8, and
wherein the high-breakdown insulating substituent group is independently selected from the group consisting of $-(CH_2)_n-CH_3$, and $-CH((CH_2)_nCH_3)_2$) where n is any number between 1 and 50, alkyl, aryl, substituted alkyl, substituted aryl, branched alkyl, branched aryl, and any combination thereof and wherein the alkyl group is selected from the group of methyl, ethyl, propyl, butyl, I-butyl and t-butyl groups, and the aryl group is selected from the group of phenyl, benzyl and naphthyl groups.

2. A capacitor comprising
a first electrode,
a second electrode, and
a crystal dielectric layer disposed between said first and second electrodes,
wherein said crystal dielectric layer comprises the energy storage molecular material according to claim 1.

* * * * *